United States Patent
Schaller

(10) Patent No.: US 10,238,534 B2
(45) Date of Patent: Mar. 26, 2019

(54) SYSTEMS AND PROCESSES FOR EYE MOISTURIZING DURING OCULAR SURGERY

(71) Applicant: Novartis AG, Basel (CH)

(72) Inventor: Philipp Schaller, Stein am Rhein (CH)

(73) Assignee: Novartis AG, Basel (CH)

( * ) Notice: Subject to any disclaimer, the term of this patent is extended or adjusted under 35 U.S.C. 154(b) by 403 days.

(21) Appl. No.: 14/167,003

(22) Filed: Jan. 29, 2014

(65) Prior Publication Data
US 2014/0257205 A1    Sep. 11, 2014

Related U.S. Application Data

(60) Provisional application No. 61/774,372, filed on Mar. 7, 2013.

(51) Int. Cl.
| | | |
|---|---|---|
| *A61F 9/00* | (2006.01) | |
| *A61F 9/008* | (2006.01) | |
| *A61F 9/007* | (2006.01) | |

(52) U.S. Cl.
CPC ............ *A61F 9/0026* (2013.01); *A61F 9/007* (2013.01)

(58) Field of Classification Search
CPC .................................. A61F 9/00; A61F 9/008
See application file for complete search history.

(56) References Cited

U.S. PATENT DOCUMENTS

| | | | | |
|---|---|---|---|---|
| 5,387,201 A | * | 2/1995 | Fowler ................ | A61M 3/0279 604/290 |
| 5,814,030 A | * | 9/1998 | Hedges, Jr. ............ | A61F 9/007 604/294 |
| 6,068,640 A | * | 5/2000 | Gordon .............. | A61B 17/3203 604/294 |
| 6,179,829 B1 | | 1/2001 | Bisch et al. | |
| 6,299,305 B1 | * | 10/2001 | Miwa ...................... | A61B 3/101 351/200 |
| 7,999,231 B2 | | 8/2011 | Iguchi et al. | |

(Continued)

FOREIGN PATENT DOCUMENTS

| | | |
|---|---|---|
| JP | 2000237135 A | 9/2000 |
| JP | 2002515802 A | 5/2002 |

(Continued)

OTHER PUBLICATIONS

Stewart, et al. Ocular Surface Disease in Patients with Ocular Hypertension and Glaucoma, Current Eye Research, vol. 36 (2011) <https://www.tandfonline.com/doi/abs/10.3109/02713683.2011.562340>.*

(Continued)

*Primary Examiner* — Benjamin Klein
*Assistant Examiner* — Sara Sass

(57) ABSTRACT

Various systems and techniques may be used for moisturizing an eye during ocular surgery. In particular implementations, a system and a technique for moisturizing an eye may include the ability to determine whether an eye should be moisturized during ocular surgery and to activate a fluid control device if an eye should be moisturized. The activation of the fluid control device may allow fluid flow from a fluid reservoir to a fluid nozzle coupled to a nozzle mounting device adapted to hold the fluid nozzle stable relative to a patient's eye. The system and the technique may also include the ability to deactivate the fluid control device.

8 Claims, 3 Drawing Sheets

(56) References Cited

U.S. PATENT DOCUMENTS

| | | | |
|---|---|---|---|
| 8,996,097 B2* | 3/2015 | Yokoi | A61B 3/101 348/78 |
| 2003/0106553 A1 | 6/2003 | Vanderveen | |
| 2003/0159141 A1* | 8/2003 | Zacharias | A61B 90/36 725/37 |
| 2007/0002274 A1* | 1/2007 | Somani | A61F 9/00 351/159.75 |
| 2008/0082078 A1* | 4/2008 | Berlin | A61F 9/00781 604/521 |
| 2010/0094232 A1* | 4/2010 | Hull | A61M 3/0279 604/290 |
| 2010/0152880 A1* | 6/2010 | Boyden | A61K 9/0019 700/117 |
| 2011/0251548 A1 | 10/2011 | Thoe et al. | |

FOREIGN PATENT DOCUMENTS

| | | | |
|---|---|---|---|
| JP | 2003250832 A | 9/2003 | |
| JP | 2004511299 A | 4/2004 | |
| JP | 2004261294 A | 9/2004 | |
| RU | 2271784 C1 | 3/2006 | |
| WO | 2009138775 | 11/2009 | |
| WO | 2012154278 A1 | 11/2012 | |
| WO | 2013020092 A1 | 2/2013 | |

OTHER PUBLICATIONS

International Search Report and Written Opinion of the International Searching Authority, International Application No. PCT/US14/15246, dated Apr. 23, 2014, 6 pages.

* cited by examiner

SYSTEMS AND PROCESSES FOR EYE MOISTURIZING DURING OCULAR SURGERY

CROSS REFERENCE TO RELATED APPLICATIONS

This application claims the benefit of U.S. Provisional Application No. 61/774,372 filed Mar. 7, 2013, the contents of both being incorporated herein by reference.

BACKGROUND

The present disclosure relates to ocular surgery, and more specifically to ocular surgery that involves intrusion into a human eye.

The human eye, in simple terms, functions to provide vision by transmitting and refracting light through a clear outer portion called the cornea and focusing the image by way of the lens onto the retina at the back of the eye. The quality of the focused image depends on many factors including the size, shape, and length of the eye, and the shape and transparency of the cornea and lens and the condition of the retina.

When trauma, age, or disease causes the lens to become less transparent, vision deteriorates because of a reduction in light transmitted to the retina. This deficiency in the eye's lens is medically known as a cataract. The treatment for this condition is often surgical removal of the lens and implantation of an artificial lens, often termed an intraocular lens (IOL).

Trauma, age, or disease may also cause the retina to peel away from its support tissue, often termed retinal detachment. Retinal detachment is more common among those with severe myopia, but may also occur as a result of physical trauma to the eye, cataract surgery, or diabetic retinopathy. Initial detachments may be localized, but without rapid treatment, the entire retina may detach, leading to vision loss and blindness.

A variety of other conditions may also require eye surgery. For example, membranes on the retina, epiretinal membrane (ERM), breaks in the internal limiting membrane (ILM), and posterior vitreous detachment (PVD) may require surgery.

To perform eye surgery, the patient's eyelids are often immobilized. This can cause the outside of the eye (e.g., the cornea) to dry out, which is detrimental to the cornea. Additionally, effluent that occurs during surgery may prevent good visibility by the surgeon into the anterior chamber of the eye. To combat these problems, an assistant (e.g., a nurse) typically moisturizes the eye undergoing surgery with a syringe filled with a saline solution.

SUMMARY

Various system and techniques for moisturizing an eye during ocular surgery are disclosed. In one general implementation, a system for moisturizing an eye during ocular surgery may include a fluid nozzle, a nozzle mounting device, a fluid reservoir, and a fluid control device. The nozzle mounting device may be adapted to hold the fluid nozzle stable relative to a patient's eye, and the fluid reservoir may be coupled to the fluid nozzle. In particular implementations, the nozzle mounting device may be a surgical microscope. The fluid reservoir may be pressurized or unpressurized. The fluid control device may be adapted to regulate fluid flow from the fluid reservoir to the nozzle for eye moisturizing. The fluid control device may, for example, include a pump.

In certain implementations, the system may include an activation device to activate the fluid control device. The activation device may, for example, include a user input device and/or a computer.

In some implementations, the fluid reservoir and the fluid control device are part of a larger system. For example, the fluid reservoir and the fluid control device may be part of a surgical console.

In another general implementation, a process for moisturizing an eye during ocular surgery may include determining whether an eye should be moisturized during ocular surgery and activating a fluid control device if an eye should be moisturized. The activation of the fluid control device may allow fluid flow from a fluid reservoir to a fluid nozzle coupled to a nozzle mounting device adapted to hold the fluid nozzle stable relative to a patient's eye. The process may also include deactivating the fluid control device.

Determining whether an eye should be moisturized during ocular surgery may include determining whether it is time to moisturize an eye. Determining whether any eye should be moisturized during ocular surgery may also include determining whether a user command to moisturize an eye has been received.

In some implementations, the process may also include determining whether to continue moisturizing the eye during ocular surgery.

Deactivating the fluid control device may, for example, include determining if an appropriate amount of fluid has flowed to the fluid nozzle. Deactivating the fluid control device may also include determining whether a user command to stop moisturize an eye has been received.

Various implementations may have one or more features. For example, moisturizing an eye during ocular surgery may prevent the cornea from being dried out, and assist a surgeon with maintaining a good view into the anterior chamber of the eye. Additionally, various implementations may be readily controlled by a user, such as according to a program and/or by manual control. Thus, a user may be able to control moisturizing of an eye undergoing ocular surgery to provide an appropriate amount of moisturizing and cleaning to the eye. Moreover, this may be under the direct control of the physician.

Various other features will be apparent to those skilled in the art from the following description and the accompanying figures.

DETAILED DESCRIPTION

Figure 1:
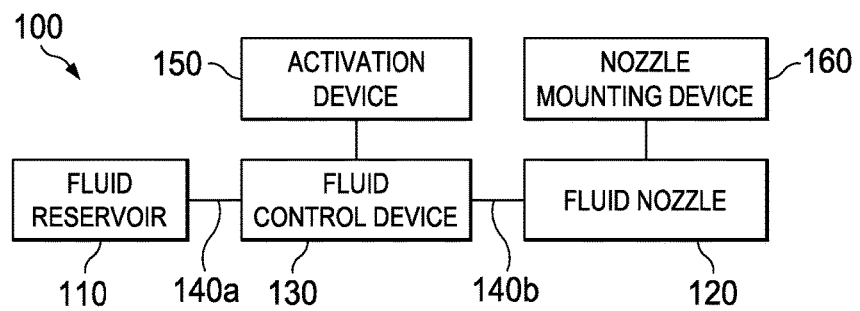
FIG. 1 is a block diagram illustrating an example system for moisturizing an eye during ocular surgery.

FIG. 1 illustrates an example system 100 for moisturizing an eye during ocular surgery. System 100 includes a fluid reservoir 110, a fluid nozzle 120, a fluid control device 130, an activation device 150, and a nozzle mounting device 160.

Fluid reservoir 110 holds the fluid to moisturize an eye. The fluid may, for example, be a water/saline solution, a viscoelastic, a water/saline solution enriched with additives (e.g., antibiotics, surfactant, topic anesthesia, or artificial tears), or any other appropriate eye moisturizing fluid. Fluid reservoir 110 may be a bottle, a bag, or any other appropriate container for a fluid and may be made of flexible plastic, hard plastic, glass, or any other appropriate material. Fluid reservoir 110 may be a standalone container or integrated into a larger system (e.g., a surgical console). In particular implementations, fluid reservoir 110 may also supply fluid for other operations during ocular surgery (e.g., to maintain intraocular pressure). The fluid in fluid reservoir 110 may be pressurized by air, gravity, and/or a pump.

Fluid nozzle 120 is adapted to eject the fluid in fluid reservoir 110 onto an eye to moisturize it. Fluid nozzle 120 may eject fluid in a spray, a stream, a jet, or any other appropriate pattern. Fluid nozzle 120 may, for example, be a needle, an injector, or any other appropriate type of fluid delivery device. In particular implementations, fluid nozzle 120 may adjustable between patterns (e.g., spray or jet). Fluid nozzle 120 may, for example, be composed of plastic, metal, glass, ceramics, or any other appropriate type of material.

Fluid control device 130 is adapted to control the flow of fluid from fluid reservoir 110 to fluid nozzle 120. Fluid control device 130 may or may not pressurize the fluid from fluid reservoir. Fluid control device 130 may, for example, be a valve, a pump, or any other appropriate device for regulating fluid flow. Fluid control device 130 may have a static or variable flow rate.

Fluid reservoir 110 is coupled to fluid control device 130 by a fluid conduit 140a, and fluid control device 130 is coupled to fluid nozzle 120 by a fluid conduit 140b. In particular implementations, fluid conduits 140 may be flexible. Fluid conduits 140 may, for example, be hoses or tubes. The hoses or tubes may be composed of rubber, plastic, or any other appropriate material. Fluid conduits 140 may be other types of devices for conveying a fluid in other implementations. In certain implementations, fluid conduit 140a and fluid conduit 140b may be the same conduit.

Activation device 150 is adapted to activate fluid control device 130. In particular implementations, activation device 150 may provide a manual activation and/or an automatic activation. If activation device 150 provides manual activation, it may, for example, include a user input device (e.g., a foot pedal, a keypad, or a touchscreen). The user input device may or may not be directly coupled to fluid control device 130. If directly coupled, the user input device may allow the user (e.g., physician or other medical professional) direct control over the fluid control device 130. If the user input device is not directly coupled to fluid control device 130, an intermediate device (e.g., a relay, a computer, and/or an actuator) may translate signals from the user input device into control signals for fluid control device 130. The intermediate device may also regulate the fluid control device (e.g., controlling how long it is active or how much fluid is ejected).

If activation device 150 provides automatic activation, it may, for example, include a computer to determine when to activate fluid control device 130. A computer may include a processor (e.g., a microprocessor, a microcontroller, an application specific integrated circuit, a field programmable gate array) and memory (e.g., electro-magnetic memory, semi-conductor memory, and/or optical memory). The processor may operate according to instructions encoded thereon and/or stored in memory. The computer may also include an input/output system to provide data to users and/or other computers and receive data from users and/or other computers. To communicate with other computers, the input/output system may include a modem, a network interface card, and/or a wireless network card. To provide data to a user, the input/output system may include a display (e.g., a screen or projector) and/or a speaker. To receive data from a user, the input/output system may include a keyboard, a mouse, a keypad, a stylus, or other input device. The components of a computer may be coupled together by one or more buses (e.g., serial or parallel).

When operating in an automatic mode, activation device 150 may determine when to activate fluid control device 130 based on a time and/or an event basis. For example, activation device 150 may be programmed to activate fluid control device 130 at a given frequency (e.g., every 30 seconds) for a given time period (e.g., between 0.5 s-1.0 s), which may vary based on fluid flow rate and droplet size. Also, activation device 150 may activate fluid control device 130 until a given amount of fluid has been ejected (e.g., a few milliliters). Additionally, activation device may deactivate the fluid control device based on a signal of a sensor (e.g., optically-based) that recognizes the dryness of the cornea.

In particular implementations, activation device 150 may allow automatic and manual modes of operation. For example, activation device 150 may follow a prescribed routine for moisturizing an eye and also allow a user to provide input to activate fluid control device 130 on demand.

Nozzle mounting device 160 mounts fluid nozzle 120 in a relatively stable position relative to an eye. Nozzle mounting device 160 may, for example, be a surgical microscope, an eye speculum, which keeps the eyelids open during surgery, or a specialized fixture. Nozzle mounting device 160 may be made of plastic, metal, or any other appropriate material. Nozzle mounting device 160 may include a bracket to mount fluid nozzle 120. In particular implementations, nozzle mounting device 160 may be adjustable to align fluid nozzle 120 with the eye.

System 100 has a variety of features. For example, system 100 may be used to moisturize an eye during ocular surgery. This may prevent the cornea from becoming dry, avoiding risk of damage to the cornea, and assist a surgeon with maintaining a good view into the anterior chamber of the eye. Additionally, system 100 may be readily controlled by a user, such as by being programmed and/or manually controlled. Thus, a user may be able to control moisturizing of an eye undergoing ocular surgery to provide an appropriate amount of moisturizing and cleaning to the eye. Moreover, moisturization of an eye may be under the direct control of the physician.

Although FIG. 1 illustrates a system for moisturizing an eye during ocular surgery, a variety of additions, deletions, substitutions, and/or modifications may be made to system 100 while still moisturizing an eye. For example, the fluid control device may be located in the fluid reservoir. As another example, the fluid reservoir and/or the fluid control device may be part of a larger system.

In particular implementations, fluid nozzle 120 may be moved into position for the moisturizing process and retracted afterwards. The fluid nozzle 120 may, for example, be moved electronically, pneumatically, magnetically, manually, or via any other appropriate technique. However, during the actual delivery of the fluid, the nozzle 120 may be held in a stable position.

Figure 2A:
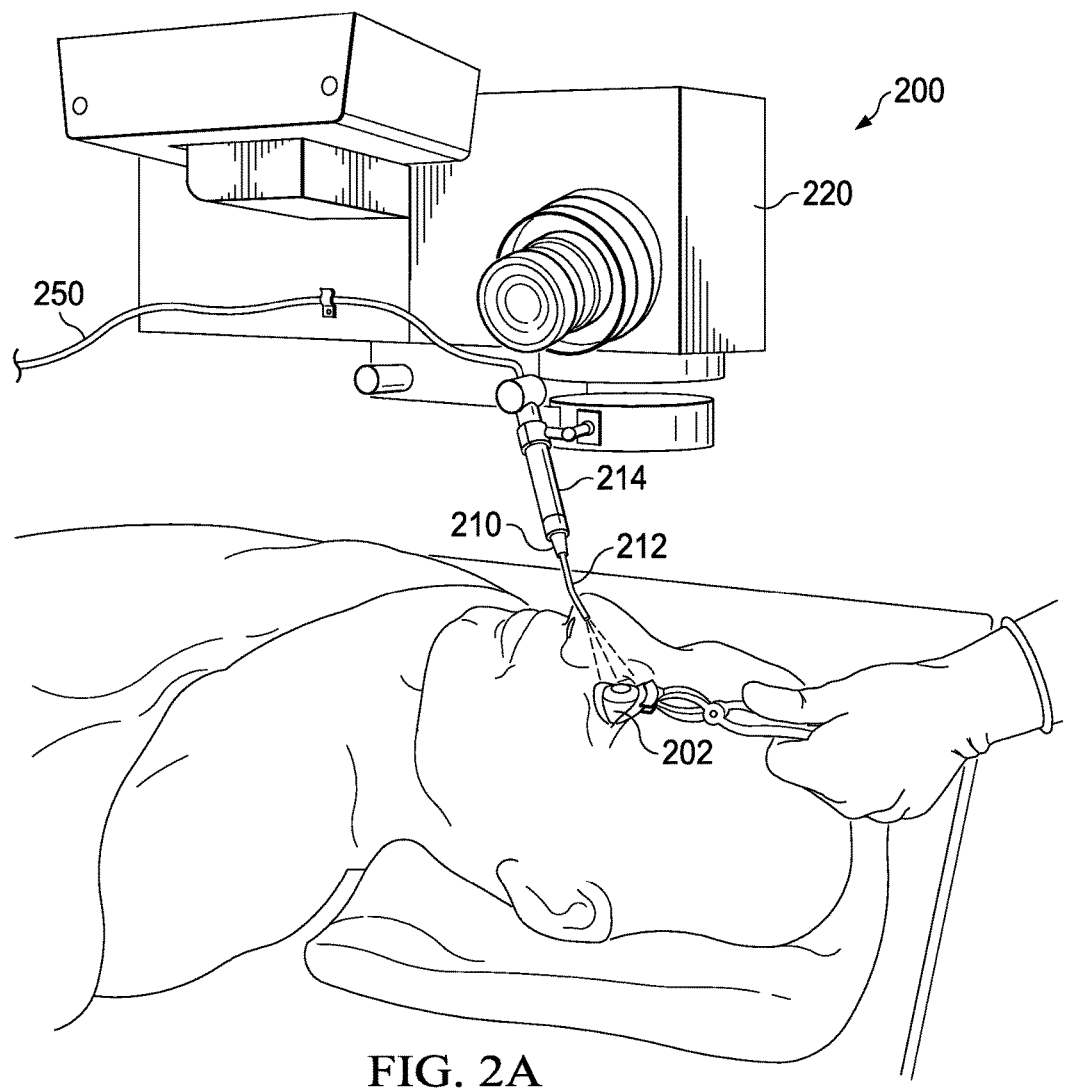
FIG. 2A shows another example system for moisturizing an eye during ocular surgery.
Figure 2B:
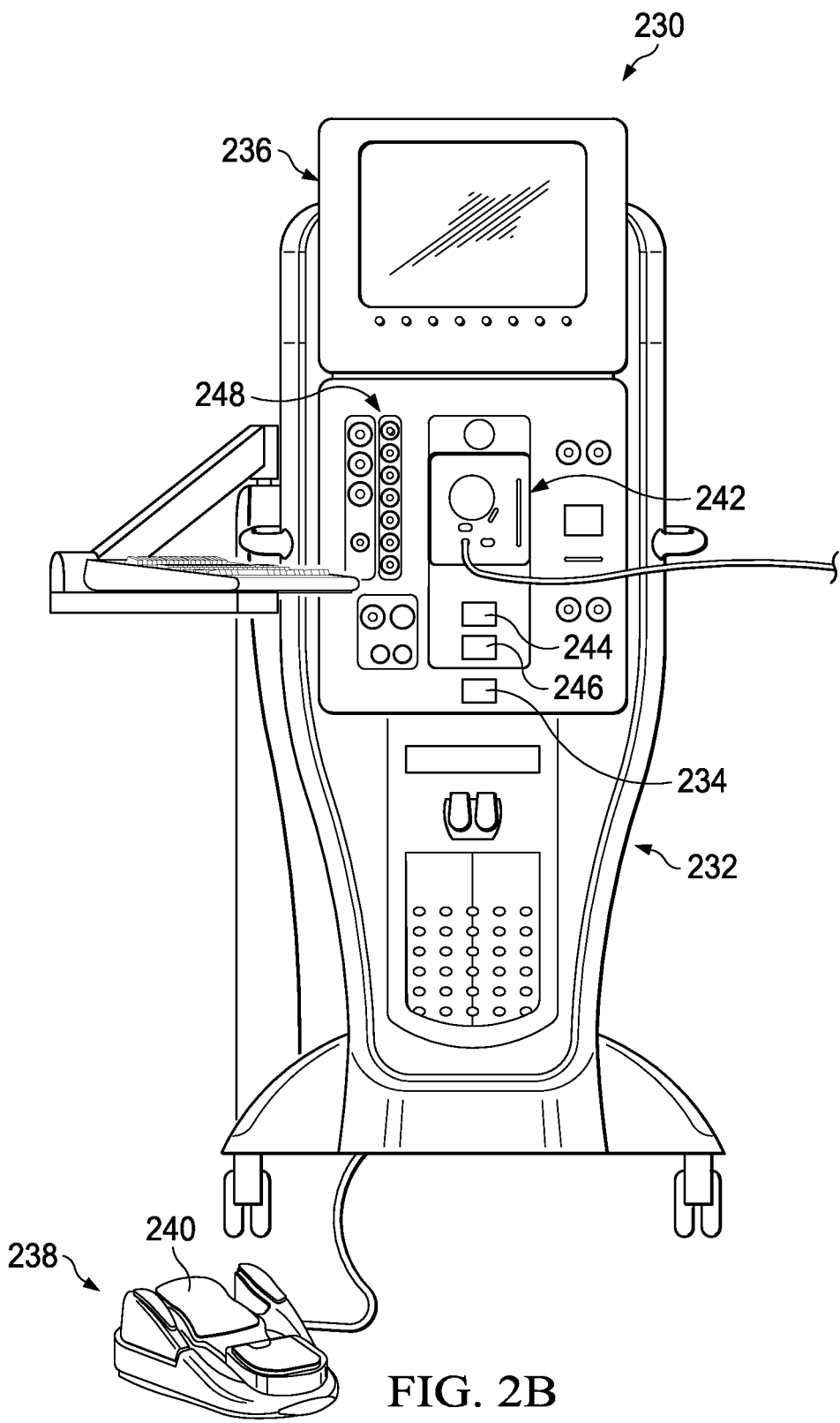
FIG. 2B shows an example surgical console that may form part of the system of FIG. 2A.

FIGS. 2A and 2B illustrate another example system 200 for moisturizing an eye 202 during ocular surgery. System 200 includes a fluid nozzle 210, a nozzle mounting device 220, and a surgical console 230.

Fluid nozzle 210 is adapted to eject fluid to moisturize the eye 202 and includes a tube 212 and a syringe 214. Syringe 214 is responsible for receiving and storing fluid to be delivered through tube 212. Tube 212 is coupled to syringe 214 and extends therefrom to deliver fluid to eye 202, such as, in a jet. Tube 212 may be composed of metal, glass, plastic, or any other appropriate material.

In FIG. 2A, nozzle mounting device 220 is a surgical microscope. However, in other implementations, the nozzle mounting device 220 may include other devices operable to secure fluid nozzle 210. Nozzle 210 may be coupled to the surgical microscope in any of a variety of manners. The surgical microscope may be positioned during ocular surgery. Nozzle 210 may be appropriately positioned by the positioning of the surgical microscope.

Referring to FIG. 2B, surgical console 230 is an example for retinal surgery console. Console 230 includes a housing 232 with a computer system 234 and an associated display 236 operable to show, for example, data relating to system operation and performance during a vitreoretinal surgical procedure. Display 236 may also interface with the console, such as to establish or change one or more operations of the console. In some instances, display 236 may include a touch-sensitive screen for interacting with the console by touching the screen of the display 236.

Various probes may be used with surgical console 230. A probe, such as, for example, a vitrectomy probe, may be coupled to console 230 for dissecting ocular tissues and aspirating the ocular tissues from the eye. Other probes may, for example, introduce fluids to and/or extract fluids from the eye. Console 230 may, for example, provide electrical, pneumatic, hydraulic, and/or other appropriate type of power to a probe. Console 230 may also be operable to control one or more functions (e.g., an infusion rate of fluid to a surgical site and/or aspiration of fluid from a surgical site), as well as to monitor one or more patient vital signs. Console 230 may also include a number of systems that are used together to perform vitreoretinal surgical procedures. For example, the systems may include a footswitch system 238 including, for example, a footswitch 240, a fluidics system 242, and a pneumatics system 248. The pneumatics system 248 may be operable to supply power to and control a probe. For example, the pneumatics system 248 may be operable to repeatedly cycle application of a pressurized gas. In some instances, the pneumatic system 248 may be operable to cycle pressurized gas at rates within the range of one cycle per minute to 7,500 cycles per minute, or possibly even 10,000 cycles per minute or more. In certain implementations, the cycled gas may be applied at, for example, different pressures, different rates, and different duty cycles. A probe may also be interfaced with console 230 via pneumatics system 248 (e.g., to control actuation of a cutter). Fluidics system 242 may be operable to provide infusion and/or irrigation fluids to the eye or a vacuum, such as to aspirate materials during a surgical procedure. To optimize performance of the different systems during surgery, their operating parameters may be varied according to, for example, the particular procedure being performed, the different stages of the procedure, the surgeon's personal preferences, whether the procedure is being performed in the anterior or posterior portion of the patient's eye, and so on.

In this implementation, fluidics system 242 includes a fluid reservoir 244 and a fluid control device 246. Fluid reservoir 244 holds the fluid to moisturize an eye. The fluid may, for example, be a water/saline solution. In particular implementations, fluid reservoir 244 may also supply fluid for other operations during an ocular surgery (e.g., to maintain intraocular pressure). Fluid control device 246 is coupled to fluid reservoir 244 and is adapted to control the flow of fluid from fluid reservoir 244 to fluid nozzle 210. Fluid reservoir 244 may, for example, be a bag, and fluid control device 246 may be a pump.

The different systems in console 230 may include control circuits for the operation and control of the various functions and operations performed by console 230, such operations of a probe. Computer system 234 may be operable to govern the interaction and relationship between the different systems to properly perform a surgical procedure. To do this, computer system 234 may include one or more processors, one or more memory devices, and may be configured or programmed to control operations of console 230, for example, based upon pre-established programs or sequences.

In certain modes of operation, fluid control device 246 operates under the control of footswitch 240 to supply fluid from fluid reservoir 244 to nozzle 210. Thus, when footswitch 240 is manipulated, fluid control device 246 supplies fluid to nozzle 210. Footswitch 240 may be indirectly coupled to fluid control device 246 (e.g., through an intermediate device).

In certain implementations, computer 234 may allow certain operations to be performed in an automatic mode. When operating in an automatic mode, computer 234 may determine when to activate fluid control device 246 based on a time and/or an event basis. For example, computer 234 may be programmed to activate fluid control device 246 at a given frequency (e.g., every 30 seconds) for a given time period (e.g., between 0.5-1.0 s), which may vary based on fluid flow rate and droplet size. Also, computer 234 may activate fluid control device 246 until a given amount of fluid has been ejected (e.g., a few milliliters).

In particular implementations, computer 234 may allow automatic and manual modes of operation. For example, computer 234 may follow a prescribed routine for moisturizing an eye and also allow a user to provide input through footswitch 240 to activate fluid control device 246 on demand.

System 200 has a variety of features. For example, system 200 may be used to moisturize an eye during ocular surgery. This may prevent a cornea from being dried out, which may damage the cornea, and assist a surgeon with maintaining a good view into the anterior chamber of the eye. Additionally, system 100 may be readily controlled by a user, such as according to a program and/or by manual control. Thus, a user may be able to control moisturizing of an eye undergoing ocular surgery, allowing an appropriate amount of moisturizing and cleaning to be applied. Moreover, this control may be under the direct control of the physician.

Figure 3:
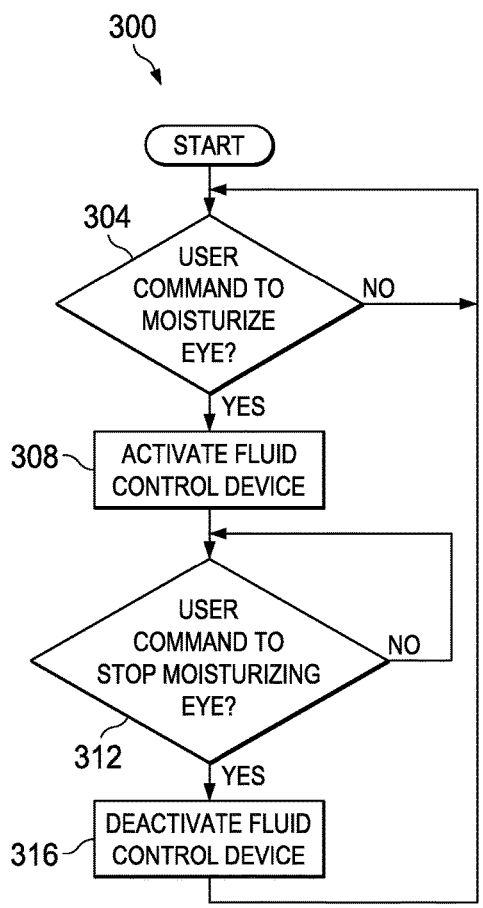
FIG. 3 is a flowchart illustrating an example process for moisturizing an eye during ocular surgery

FIG. 3 illustrates an example process 300 for moisturizing an eye during ocular surgery. Process 300 may, for example, be implemented by a system similar to system 100 or 200. Other eye moisturizing systems may also implement the process.

Process 300 calls for determining whether a user command to moisturize an eye has been received (operation 304). Determining whether a user command has been received may, for example, be accomplished by detecting a signal (e.g., electrical or pressure) from a user input device (e.g., a foot pedal, a keypad, or a touchscreen). If a user command to moisturize an eye has not been received, process 300 calls for continuing to wait for the command.

Once a command to moisturize an eye has been received, process 300 calls for activating a fluid control device (operation 308). A fluid control device may, for example, be a valve or a pump and activating the device may include adjusting a configuration of the fluid control device (e.g., placing the fluid control device in an open position) or by adjusting an operational mode of the fluid control device (e.g., running the fluid control device). Process 300 also calls for determining whether a user command to stop moisturizing an eye has been received (operation 312). Determining whether a user command has been received may, for example, be accomplished by detecting a signal (e.g., electrical or pressure) from a user input device (e.g., a foot pedal, a keypad, or a touchscreen). If a user command to stop moisturizing an eye has not been received, process 300 calls for continuing to wait for the command.

Once a command to stop moisturizing an eye has been received, process 300 calls for deactivating the fluid control device (operation 316). A fluid control device may, for example, be a valve or a pump and deactivating the device may include adjusting a configuration of the fluid control device (e.g., placing the fluid control device into a closed position) or by adjusting an operational mode of the fluid control device (e.g., shutting off the fluid control device).

Although FIG. 3 illustrates an example process for moisturizing an eye, other processes for moisturizing an eye may include fewer, additional, and/or a different arrangement of operations. For example, a process may not include determining whether a user command to stop moisturizing an eye has been received. This may occur, for instance, when a fluid control device has an active time (e.g. a few seconds) or fluid volume (e.g., a few milliliters) associated with it. As another example, a process may include determining whether to moisturize an eye. This may, for example, occur when an automated device is involved with moisturizing an eye.

Figure 4:
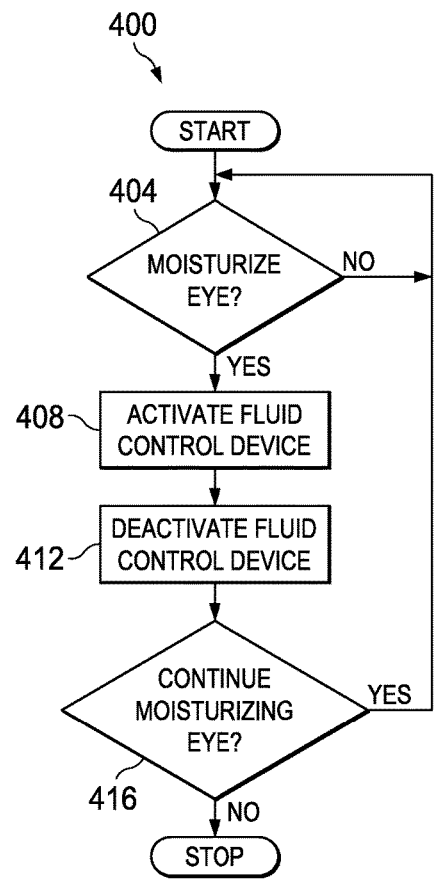
FIG. 4 is a flowchart illustrating another example process for moisturizing an eye during ocular surgery.

FIG. 4 illustrates another example process 400 for moisturizing an eye during ocular surgery. Process 400 may, for example, be implemented by a system similar to system 100 or 200. Other eye moisturizing systems may also implement the process.

Process 400 calls for determining whether to moisturize an eye (operation 404). Determining whether to moisturize an eye may, for example, be accomplished by determining whether a time period has expired. During an eye surgery, an eye may be need to be moisturized on a fairly regular basis (e.g., every 30 seconds). If an eye should not be moisturized, process 400 calls for waiting until the eye should be moisturized.

Once it is time to moisturize an eye, process 400 calls for activating a fluid control device (operation 408). A fluid control device may, for example, be a valve or a pump and activating the device may include adjusting a configuration of the fluid control device (e.g., placing the fluid control device in an open position) or by adjusting an operational mode of the fluid control device (e.g., running the fluid control device).

Process 400 also calls for deactivating a fluid control device (operation 412). A fluid control device may, for example, be a valve or a pump and deactivating the device may include adjusting a configuration of the fluid control device (e.g., adjusting the fluid control device into a closed position) or by adjusting an operational mode of the fluid control device (e.g., shutting off the fluid control device). Determining whether to deactivate the fluid control device may, for example, be based on time, fluid flow, or a signal of a sensor (e.g., optically-based) that recognizes the dryness of the cornea.

Process 400 also calls for determining whether to continue moisturizing an eye (operation 416). Determining whether to continue moisturizing an eye may, for example, be based on time or receiving a user input to stop moisturizing an eye (e.g., at the end of a surgery).

If an eye should not continue to be moisturized, process 400 is at an end. If an eye should continue to be moisturized, process 400 calls for again determining whether to moisturize the eye (operation 404).

Although FIG. 4 illustrates one implementation of a process for moisturizing an eye, other processes for moisturizing an eye may include fewer, additional, and/or a different arrangement of operations. For example, a process may include determining whether a user command to moisturize an eye has been received. Thus, a process may include automated moisturizing of an eye and manual moisturizing of an eye. As another example, a process may include determining whether to deactivate a fluid control device. This may, for example, be based on time or fluid flow.

The various implementations discussed and mentioned herein have been used for illustrative purposes only. The implementations were chosen and described in order to explain the principles of the disclosure and the practical application and to allow those of ordinary skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

Various systems and processes for moisturizing an eye during ocular surgery have been discussed, and several others have been mentioned or suggested. However, those skilled in the art will readily recognize that a variety of additions, deletions, substitutions, and modifications may be made to these systems and processes while still achieving eye moisturizing. Thus, the scope of protection should be judged based on the following claims, which may capture one or more aspects of one or more implementations.

The invention claimed is:

1. A system for moisturizing an eye during ocular surgery, the system comprising:
   a fluid nozzle;
   a nozzle mounting device adapted to hold the fluid nozzle stable relative to a patient's eye;
   a fluid reservoir coupled to the fluid nozzle;
   a fluid control device adapted to regulate fluid flow from the fluid reservoir to the nozzle for eye moisturizing; and
   an activation device operable to activate and to deactivate the fluid control device, wherein the activation device comprises a computer and is operable to activate the fluid control device at a given time frequency or at an occurrence of an event,
   wherein the fluid control device comprises a computer operable to control an amount of fluid dispensed by the fluid control device,
   wherein the activation device comprises a sensor operable to detect a dryness level of a cornea of an eye, and wherein the activation device is operable to deactivate the fluid control device in response to a dryness of the cornea of the eye.

2. The system of claim 1, wherein the fluid control device comprises a pump.

3. The system of claim 1, further comprising an activation device to activate the fluid control device.

4. The system of claim 3, wherein the activation device comprises a user input device.

5. The system of claim 1, wherein the fluid reservoir is pressurized.

6. The system of claim 1, wherein the nozzle mounting device comprises a surgical microscope.

7. The system of claim 1, wherein the fluid reservoir and the fluid control device are part of a surgical console.

8. The system of claim 1, wherein the fluid reservoir comprises a bottle or bag.

\* \* \* \* \*